ABSTRACT
United States Patent [19]
Halperin et al.

[11] Patent Number: 4,928,674
[45] Date of Patent: May 29, 1990

[54] CARDIOPULMONARY RESUSCITATION AND ASSISTED CIRCULATION SYSTEM

[75] Inventors: Henry Halperin, Baltimore; Joshua Tsitlik, Reisterstown; Myron Weisfeldt, Baltimore; Mark Gelfand, Reisterstown, all of Md.

[73] Assignee: The Johns Hopkins University, Baltimore, Md.

[21] Appl. No.: 273,810

[22] Filed: Nov. 21, 1988

[51] Int. Cl.$^5$ .............................................. A61H 31/00
[52] U.S. Cl. ...................... 128/30.2; 128/28; 128/683; 128/685; 128/419 D; 128/697
[58] Field of Search ............... 128/28, 679, 30.2, 327, 128/681–683, 685, 419 D, 697; 600/16

[56] References Cited

U.S. PATENT DOCUMENTS

| | | | |
|---|---|---|---|
| 2,869,537 | 1/1959 | Jen-Chu Chu | 128/30.2 |
| 4,077,400 | 3/1978 | Harrigan | 128/28 |
| 4,349,015 | 9/1982 | Alferness | 128/28 |
| 4,664,098 | 5/1987 | Woudenberg et al. | 128/30.2 |

Primary Examiner—Francis Jaworski
Assistant Examiner—George Manuel
Attorney, Agent, or Firm—Cushman, Darby & Cushman

[57] ABSTRACT

A vest system for generating cyclic fluctuations in intrathoracic pressure for use in cardiopulmonary resuscitation and non-invasive circulatory assistance. The vest is preferably provided with a two bladder inflation system. A high pressure bladder contacts the chest wall while a bias bladder is disposed between the high pressure bladder and the vest material. The bias bladder is pressurized to press the high-pressure bladder tightly against the chest wall so that cyclic inflation of the high-pressure bladder can generate large changes in intrathoracic pressure. The bias bladder is released periodically to allow the chest to expand for adequate ventilation. Air flow into and out of each bladder is controlled by sequencing large bore 3-way and 2-way solenoid valves and the rate of air flow into the high-pressure bladder is controlled by a variable resistor.

30 Claims, 6 Drawing Sheets

Valves B,C-Normaly Closed
Valve A-Normaly Open

FIG. 7

| Prediction | Combined | B Bladder | HP Bladder | Assistance | Ventilation |
|---|---|---|---|---|---|
| ON | ON | ON | ON | OFF | ON |

|  |  | OLD | NEW | REAL |
|---|---|---|---|---|
| RATE | (/min) | 60 | 60 |  |
| DUTY CYCLE | ( % ) | 50 | 50 |  |
| START TIME | ( % ) | 0 | 0 |  |
| INFLATION | ( ms ) | 110 | 110 | 112 |
| VACUUM | ( ms ) | 200 | 200 |  |
| PRESSURE | (mm Hg) | 190 | <u>190</u> | 195 |
| VENT.DURATION | ( ms ) | 500 | 500 |  |
| VENT.START | ( % ) | 5 | 5 |  |

|  |  |  |  |  |
|---|---|---|---|---|
| RATE | (/min) | 60 | 60 |  |
| DUTY CYCLE | ( % ) | 50 | 50 |  |
| START TIME | ( % ) | 0 | 0 |  |
| INFLATION | ( ms ) | 40 | 40 |  |
| VACUUM | ( ms ) | 200 | 200 |  |
| PRESSURE | (mm Hg) | 15 | <u>15</u> | 18 |
| RELEASE RATE | (cyc) | 5 | 5 |  |

| COMBINED | B.BLAD | CHANGE | HP.BLAD | PREDICT | SYNCHRO | ASSIST | VENT. |
|---|---|---|---|---|---|---|---|
| A | B | C | D | E | F | G | H |

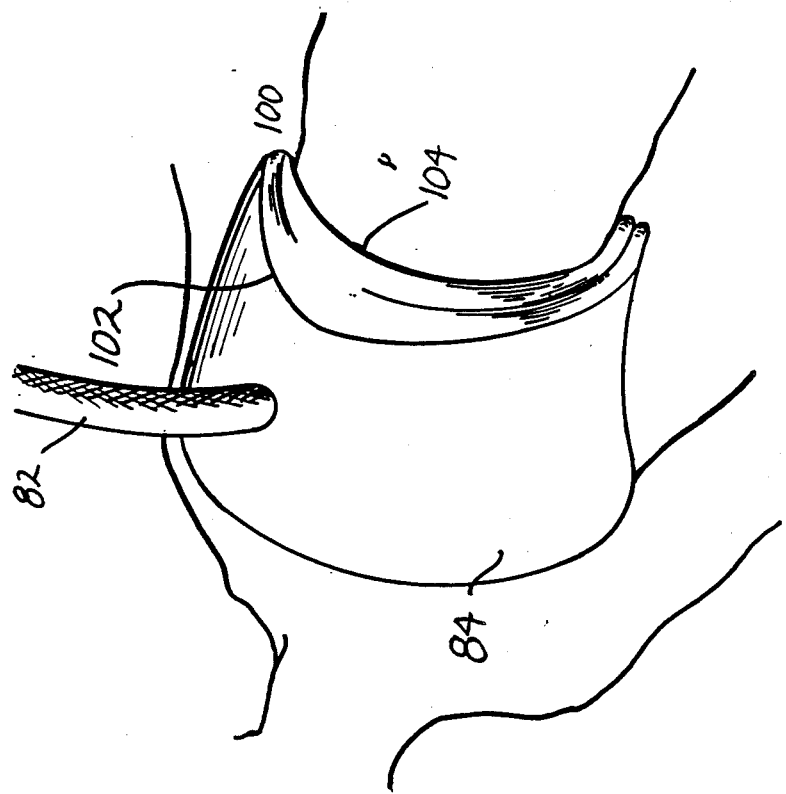
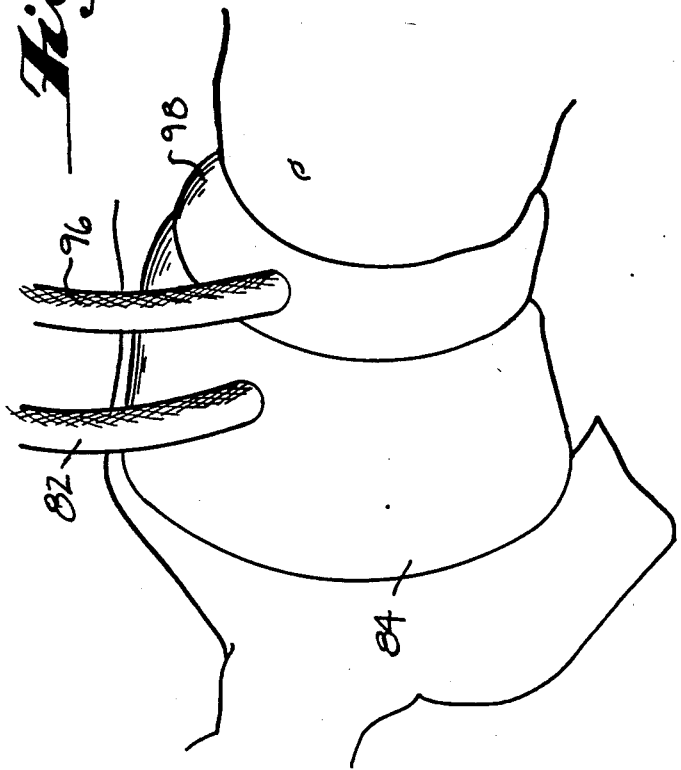
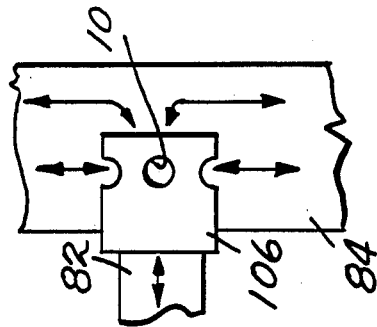

CARDIOPULMONARY RESUSCITATION AND ASSISTED CIRCULATION SYSTEM

BACKGROUND OF THE INVENTION

1. Field of the Invention

The present invention relates to cardiopulmonary resuscitation and, in particular, to a system for generating cyclic fluctuation in intrathoracic pressure for use in cardiopulmonary resuscitation and non-invasive circulatory assistance.

2. Description of The Related Art

Cardiac arrest is generally due to ventricular fibrillation, which causes the heart to stop pumping blood. The treatment of ventricular fibrillation is defibrillation. If, however, more then a few minutes have lapsed since the onset of ventricular fibrillation, the heart will be sufficiently deprived of oxygen and nutrients such that defibrillation will generally be unsuccessful. Thus, it is necessary to restore flow of oxygenated blood to the heart muscle by cardiopulmonary resuscitation in order for defibrillation to be successful.

It is known that fluctuations in intrathoratric pressure can produce blood flow during cardiopulmonary resuscitation. Thus, efforts have been made to increase intrathoratric pressure to levels above those obtained conventionally in order to produce increased blood flow. For example, high-pressure ventilation has been used with simultaneous mechanical sternal compression or circumferential thoracic compression with an inflatable vest, to increase the levels of intrathoratric pressure generated. However, such techniques have required endotrachacheal intubation and this invasive technique and the simultaneous high-pressure ventilation have presented high risks to the patient and are cumbersome and time consuming and thus have limited usefulness.

In accordance with a technique of circulatory support intrathoracic pressure changes phase locked to the cardiac cycle have been used to assist the failing but still beating heart. These intrathoracic pressure changes have been generated either by lung pressurization simultaneous with chest compression or by lung pressurization with the chest bound to prevent thoracic expansion. In all cases, then, pressurization of the lungs was required to produce adequate changes in intrathoracic pressure.

Furthermore, we previously developed a system that could generate large changes in intrathoracic pressure without simultaneous ventilation. That system used a thoracic vest that was rapidly inflated and deflated. However, the vest had to be applied to the patient so that it was extremely tight about the chest and had to be positioned very accurately in order for it to function properly. Therefore, because the vest had to be attached so tightly it compromised ventilation and the tightness and positioning requirements made it very difficult for the vest to be applied correctly. If the vest was not applied correctly, higher pressures in the vest had to be used in order to obtain a given level of intrathoracic pressure. Higher vest pressures however would lead to excessive trauma to the patient thereby compromising resuscitation.

As is apparent from the foregoing it can be appreciated that the success of resuscitation is directly related to the generated intrathoracic pressure and inversely related to the amount of trauma produced.

As noted above the earlier techniques requiring endotracheal intubation were difficult to apply properly and the high-pressure ventilation of the lungs could damage them. Furthermore, our earlier system produced inconsistent levels of intrathoracic pressure during assistance of a beating heart if the heart rate was irregular. These inconsistent levels of intrathoracic pressure could result in pressures that were far too low for adequate assistance or that were high enough to cause excessive trauma.

It would therefore be desirable to provide a system which can generate high levels of intrathoracic pressure without the need for simultaneous ventilation through endotracheal intubation. Preferably, such a system would generate a maximum fluctuation in intrathoracic pressure, adequate ventilation and would be safe to the patient and easy to implement.

SUMMARY OF THE INVENTION

It is an object of the present invention to provide a system for cardiopulmonary resuscitation which can generate maximum fluctuations in intrathoracic pressure and adequate ventilation without requiring endotracheal intubation.

The foregoing object is realized in accordance with the present invention by providing a pneumatic vest that is placed around the thorax and a particular inflation system. The vest must tightly contact the thorax in order to generate maximum fluctuations in intrathoracic pressure. On the other hand, for adequate ventilation the vest must be loose. In order to achieve both these divergent goals, a vest having two inflation bladders is preferably provided in accordance with the invention. One bladder, a high-pressure bladder, contacts the chest wall covering the front of the chest and extending laterally to the sides while the other bladder, a bias or urging bladder, is between the high-pressure bladder and the vest itself. The bias bladder is pressurized to press the high-pressure bladder tightly against the chest wall so that cyclic inflation of the high-pressure bladder can produce large changes in intrathoracic pressure, while minimizing air movement. Pressure in the bias bladder is released periodically to allow adequate ventilation to occur.

It has further been found that the divergent design goals noted above can be achieved with a one-bladder vest system. Indeed, where the pressure in the bladder is clamped above atmospheric pressure during the deflation portion of cycles without ventilation. During ventilation, however, pressure is totally released. With either system, the timing of vest inflation and deflation can be fixed for use during resuscitation when the heart is not beating. Vest inflation can also be synchronized to an external signal, for example, a processed electrocardiograph, to assist a failing but still beating heart.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

BRIEF DESCRIPTION OF THE DRAWINGS

FIG. 7 shows an example of a display of inputs to the system;

FIG. 10 is a perspective view of another vest provided in accordance with the present invention;

FIG. 11 is a schematic perspective view of yet another vest provided in accordance with the present invention; and FIG. 12 is a schematic elevational view partly in cross-section showing a coupling of an air-hose to a bladder provided in accordance with the present invention.

DETAILED DESCRIPTION OF THE PRESENTLY PREFERRED EXEMPLARY EMBODIMENT

Figure 1:
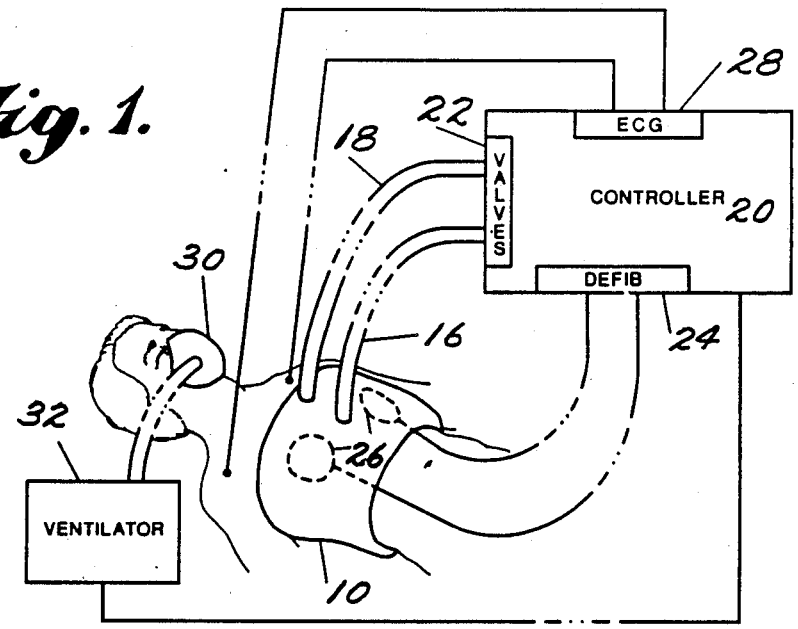
FIG. 1 is a schematic perspective view of a two bladder vest system formed in accordance with the present invention.
Figure 2:
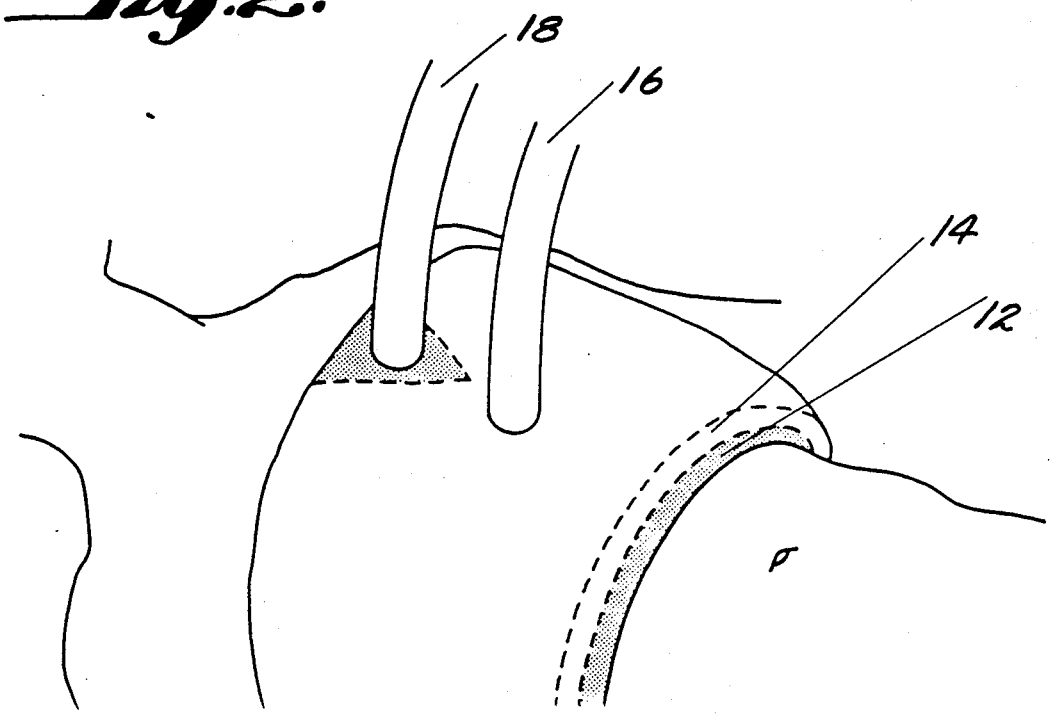
FIG. 2 is an enlarged schematic perspective view of the vest shown in FIG. 1.

A schematic illustration of the two-bladder vest system is shown in FIG. 1, and details of the vest 10 are shown more clearly in FIG. 2. The high-pressure bladder 12 and bias or urging bladder 14 sit on top of each other and are incorporated into a vest 10 which surrounds the thorax. Each bladder can be inflated and is analogous to a large blood pressure cuff. The bladders are connected by large-bore hoses 16, 18 to a controller 20.

Controller 20 has valves 22 that are sequenced by a microcomputer to inflate and deflate each bladder. Controller 20 also has a defibrillator 24 that can be used to deliver a defibrillating pulse to electrodes 26 on the surface of the thorax. An electrocardiogram (ECG) processor 28 receives electrical signals from the thorax and is used during circulatory assistance to synchronize vest inflation and deflation to the beating heart, as described more fully below. A face mask 30 or other appropriate connection system is used to direct oxygen-enriched air into the patient's lungs from a ventilator 32. Ventilator 32 can be started and stopped by controller 20. It is to be understood, however, that the ventilation is necessary only for delivery of oxygen, not for generation of intrathoracic pressure. Therefore, an endotracheal tube does not have to be used.

Figure 3:
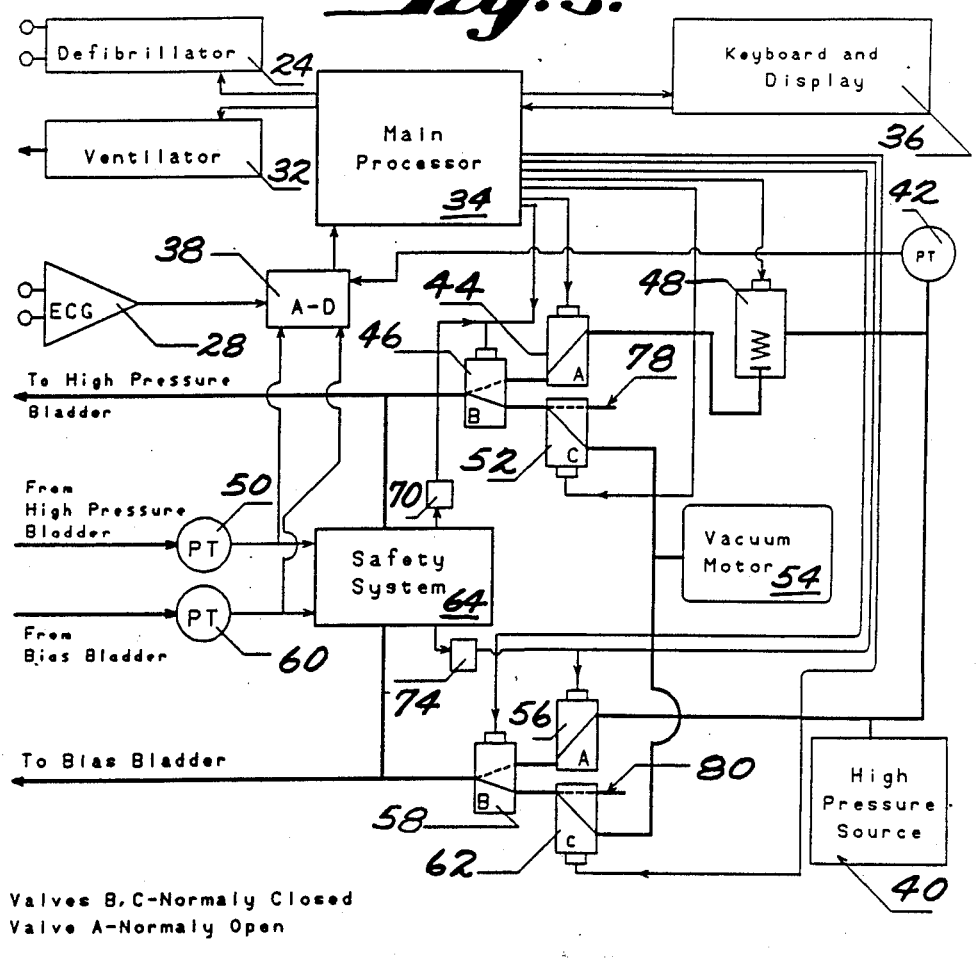
FIG. 3 schematically depicts the controller of the present invention.

Referring to FIG. 3, the controller 20 has defibrillator 24, electrocardiogram processor 28, and ventilator 32, as noted above. The main processor 34 is a programmable logic unit that has program memory, data memory, internal registers, interfaces to various peripherals, and is capable of various arithmetic and logic operations. A keyboard and display 36 are used to input desired operating parameters and to output actual operating conditions. An analog-to-digital (A-D) converter 38 is used to convert analog pressure signals and analog electrocardiogram signals to binary numbers that can be operated on by the processor. The pressure of the high-pressure air source 40 is measured by a pressure transducer 42.

Under control of the main processor, high-pressure air flows into the high-pressure bladder through normally-open, two-way valve A 44, and normally-closed, three-way valve B 46. The rate of air-flow into the bladder is controlled by a variable resistor 48. Pressure in the bladder is measured by a pressure transducer 50. Air flows out of the high-pressure bladder through valve B 46, and normally-closed, three-way valve C 52 to exhaust 78. Air-flow out of the bladder is facilitated by negative pressure from a vacuum motor 54.

Similarly, high-pressure air flows into the bias bladder under control of the main processor through a normally-open, two-way valve A 56, and normally-closed, three-way valve B 58. Pressure in the bladder is measured by a pressure transducer 60. Air flows out of the bias bladder through valve B 58 and normally-closed, three-way valve C 62 to exhaust 80. Air-flow out of this bladder is also facilitated by negative pressure from a vacuum motor 54. Air flow to each bladder of the vest is controlled by the proper sequencing of the respective A, B, and C valves shown in FIG. 3.

Figure 4:
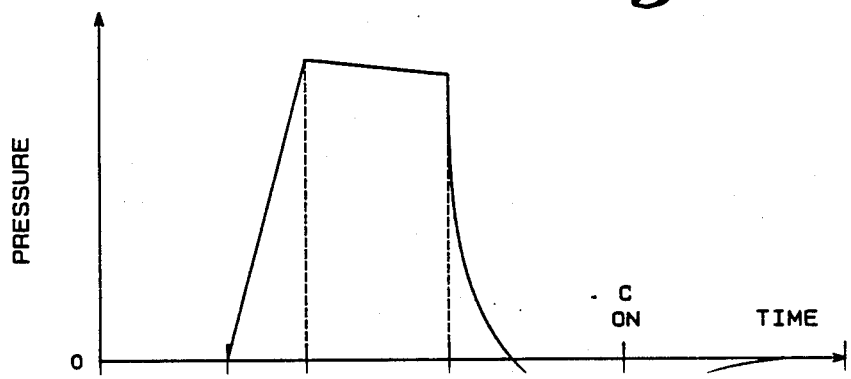
FIG. 4 shows the timing of the valves of the system of the invention.

The timing of the valves for one bladder is shown in FIG. 4. At the start of the cycle, valves A and B are released (OFF) and valve C is actuated (ON). At the start of inflation, valve B is actuated allowing high-pressure air to flow into the vest. At the end of inflation, valve A is actuated to clamp pressure in the vest. At the start of deflation (end of Compression Duration), all valves are released, which has the effect of applying a vacuum to the bladder while at the same time blocking the flow of high pressure air. At the end of the vacuum time, valve C is actuated which connects the bladder to atmosphere through the exhaust.

This somewhat complicated sequence of events is necessary to accomplish a number of objectives. First, a rapid rise in pressure in the bladder is needed in order to achieve large rises in intrathoracic pressure. This is accomplished by having a high pressure air source (50-70 psi) and using two valves (A,B) to control high pressure air. The solenoid valves actuate more rapidly than they release, so that better control can be obtained if both the starting and stopping of high-pressure airflow is controlled by valve actuation. Second, a rapid deflation is desired. This rapid deflation is accomplished by connecting the bladder to vacuum at the start of deflation. Maintenance of vacuum for longer than it takes to deflate the bladder is not desirable, however, because inflation would subsequently start at a lower pressure and require more air. The application of atmospheric pressure to the bladder through the exhaust prior to inflation assures that inflation will start with the bladder near atmospheric pressure.

Excessive peak pressures in the bladder have been shown to cause significant trauma. All previous systems of which applicants are aware have had deficiencies in controlling the peak pressure, as well as deficiencies in reducing vest pressure if an over-pressure state occurs. The system of the invention has a number of features that assure that the proper peak pressure is obtained under normal working conditions, and that over-pressure states do not occur, even if there has been the failure of a component.

Figure 5:
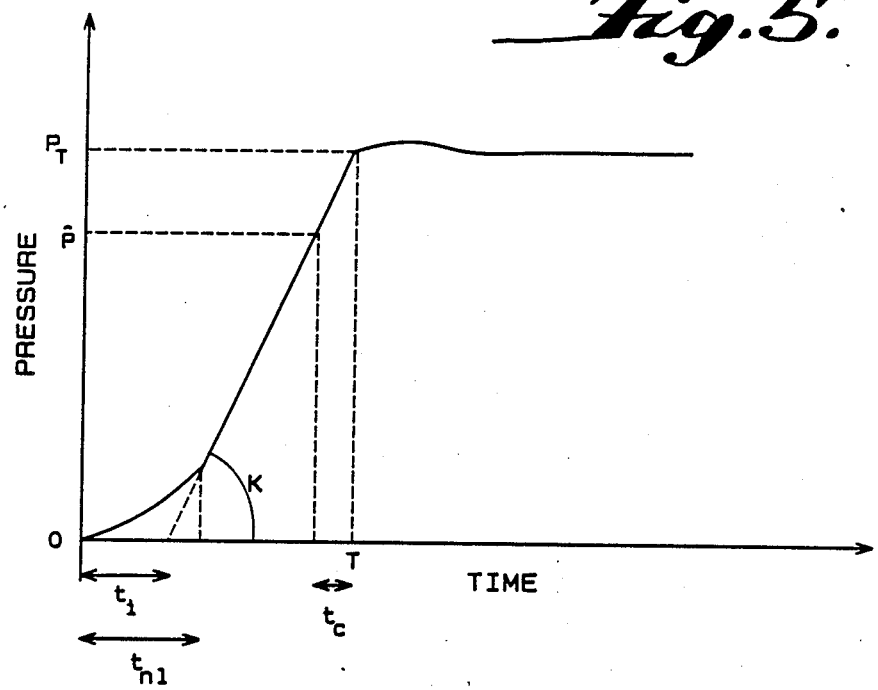
FIG. 5 is a graphical representation of bladder pressure over time.

The proper peak pressure is obtained by feed-forward and feedback control. The feed-forward control is in the form of an algorithm that examines the pressure in each bladder as it rises during inflation (FIG. 5) and predicts when to actuate the clamping valve (Valve A, FIG. 3) in order to achieve the desired peak pressure. The rise in pressure in each bladder is fairly linear after an initial non-linear portion. The time duration of this non-linear portion is represented by $t_{nl}$. The pressure during the subsequent linear portion of the pressure rise can be represented by:

$$p = K \cdot (t - t_i)$$

where p is the measured pressure at time t after the opening of the inflation valve (Valve B, FIG. 3), K is the slope of the rise in pressure, and $t_i$ is the time intercept of linear pressure rise. The desired pressure $P_T$ will be attained at time T, when the clamping valve mechanically closes. Since there is a delay ($t_c$) in the mechanical closing of the clamping valve after the electrical clamping command occurs, it is necessary to issue the electrical clamping command at a time $t_c$ before the desired pressure $P_T$ occurs. The pressure will rise by $K \cdot t_c$ after the electrical clamping command occurs, so that it is only necessary to issue the clamping command at a time when:

$$p = P = P_T - K \cdot t_c + w$$

where w is a feedback term that is used to correct inaccuracies in the prediction. The processor samples the pressure in each bladder every 4 ms, and computes a new K during each sample, where K is simply the sum of the increments in rise in pressure from each sample divided by the number of samples. The value of K is related to the pneumatic resistance between the high-pressure air source and the bladder. For the high-pressure bladder, this resistance is primarily determined by a variable resistor 48 (FIG. 3), which is changed between inflations to achieve the desired time of inflation. With the above prediction method, applicants have found that peak pressures within 5% of those desired are easily achieved and, by varying the high-pressure bladder's resistor, inflation times within 10% of those desired can be achieved. This inflation method is sufficient to assure that proper peak bladder pressures are obtained under normal operating conditions. If, however, a failure of the hardware or software should occur, an independent safety system, described more fully below is present to prevent over-pressurization of the bladders.

Figure 6:
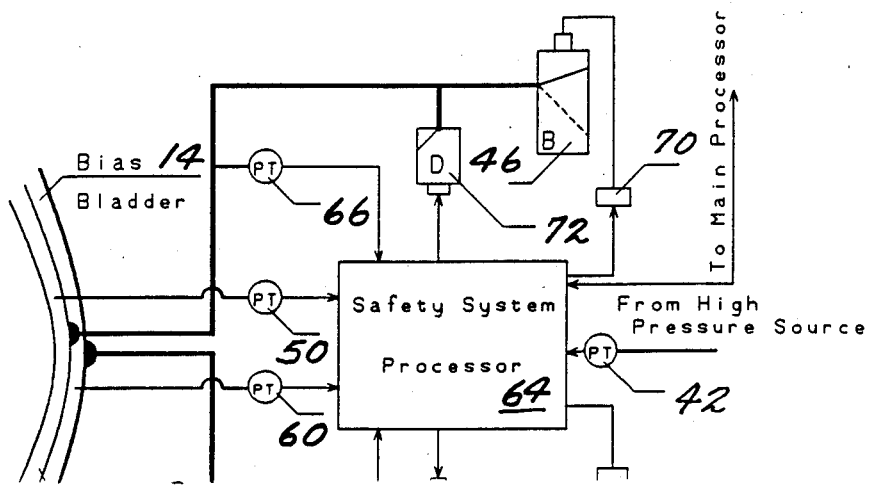
FIG. 6 schematically illustrates the safety system of the invention.

The safety system 64 (FIG. 3; FIG. 6) monitors the level of pressure and the amount of time that pressure is present in each bladder and thus assures that excessive pressure is not present in the bladders even if there is a failure in the main system. Further, the safety system tests itself on power-up to be sure it is operative. The safety system processor itself is a programmable logic unit, incorporating interfaces to valves, a communication link to the main processor, and an analog-to-digital converter for digitizing pressures. More particularly, the safety system processor monitors the pressure in the bias and high-pressure bladders 14, 12 via the main systems' transducers 60, 50. The safety system also measures the pressures in the air lines to each of these bladders via separate transducers 66, 68.

If the safety system processor detects a pressure in the high-pressure bladder 12 that is above a pre-programmed limit on amplitude or duration, or if the pressures measured by transducers 50 and 66 are different, it releases the high-pressure bladder's valve B 46 by a switch 70 and also releases its actuated, normally-open valve D 72. The effect is to vent pressure from the bladder and block any high-pressure air from entering the bladder. This effect is the same as would occur during a power loss.

Likewise, if the safety system processor detects a pressure in the bias bladder 14 that is too high or lasts too long, or if the pressures measured by transducers 60 and 68 are different, it releases the bias bladder's valve B 58 by a switch 74, and also releases its actuated, normally-open valve D 76. The safety system 64 also monitors the pressure of the pressure air source 40, and will stop operation if it is outside of proper limits. The main system also monitors the pressures in the bladders and can vent the bladders to atmosphere if pressures are too high or last too long. Since the two systems are independent, the only way that over-pressurization of a bladder could persist would be the unlikely event that both the main system and safety system failed.

The program that controls the inflation/deflation system has a foreground and background. The foreground controls the keyboard and display, while the background is an interrupt routine that is entered every 4 ms. The background routine calculates values for the pressure prediction algorithm, detects external synchronization pulses, controls the actuation and release of the valves, and varies the resistor 48 in the line to the high-pressure bladder 12.

The desired operating parameters for the system are input to the system via the keyboard and are shown on the display. An example of the display is shown in FIG. 7, and illustrates the parameters that are controlled. The display has four major parts. The upper box has parameters for the high-pressure bladder 12, while the lower box has parameters for the bias bladder 14. The items (A-H) on the lower two lines of the screen are a menu of operating mode toggles. Selecting the item sequentially turns that mode on and then off, except for "C" which updates the parameters. The current status of the modes is shown on the upper two lines of the screen.

Values for the parameters are input at the display cursor (underline), which initially is located in one row of the column marked "NEW". The desired parameter is selected by moving the cursor via the cursor control keys (up or down) to its row. Values are then entered at the keyboard, terminated with a C/R, and are displayed in the "NEW" column. Values in the "NEW" column become the control parameter values when a "C" is pressed. The program then updates the display by moving all of the values in the "NEW" column to the "OLD" column. This scheme allows the new parameter values to be set up while current parameter values are operative. The new parameter values will be activated at the start of the next cycle. This type of change-over is necessary so that resuscitation or assist will not be interrupted. When the program updates the display, it also calculates the actuation and release times for each valve and stores those times in memory for use by the background. Actual values of the control parameters are displayed in the "REAL" column.

The control parameters are as follows: "RATE" is the number of cycles per minute. "START TIME" is the time into the cycle for the start of inflation, expressed as a percent of the cycle period. The variable START TIME allows variable phasing of other events with respect to the start of inflation. "DUTY CYCLE" is the percentage of the cycle that high-pressure is present in the bladder, i.e. 100 times the compression duration divided by the cycle period. "INFLATION" is the amount of time that high-pressure air flows into a bladder. The "INFLATION" time is set by the prediction algorithm, but can be determined by the operator if the prediction algorithm is disabled. "VACUUM" is the length of the vacuum phase of the cycle. "PRESSURE" is the desired peak pressure. The actual measured peak pressure will be displayed in the "REAL" column. "VENT.DURATION" is the amount of time that ventilation will occur, once ventilation has started. "VENT.START" is the time into the cycle that ventilation will start, expressed as a percentage of the cycle. "RELEASE RATE" is the number of high-pressure cycles that occur before one ventilation.

The operating modes are as follows: The high-pressure bladder ("HP.BLAD") is activated by "D", while the bias bladder ("B.BLAD") is activated by "B". The "B" and "D" modes allow either bladder to be used separately or together. With both bladders activated and "SYNCHRO (F)" OFF, the cycle rates of each bladder are equal to those that were entered for each bladder separately. With "SYNCHRO" ON, however, the cycle rate for both bladders is determined by the rate entered for the high-pressure bladder. The "COMBINED (A)" mode optimizes ventilation while still allowing large changes in intrathoracic pressure to be generated. In the "COMBINED" mode, the bias bladder is inflated to a constant low pressure (5–30 mm Hg) to press the high-pressure bladder tightly against the chest wall. The high-pressure bladder is cycled 40–180 times/min to peak pressures of 70–350 mm Hg. The tightness allows large changes in intrathoracic pressure to be generated. After a set number of high-pressure cycles ("RELEASE RATE"), the bias bladder is deflated and ventilation occurs while both bladders are deflated. With both bladders deflated, there is the least amount of compressive force on the chest wall, and the lungs can be most fully expanded, yielding the most efficient ventilation. The peak-pressure-prediction algorithm is automatically activated in the "COMBINED" mode, but can be activated in all other modes by "PREDICT (E)". In all modes except "COMBINED", ventilation can occur during each cycle. Ventilation is activated or deactivated with "VENT (H)". The "ASSIST (G)" mode allows for synchronization of the controller with an external event, where the cycle length is the time between two external sync pulses.

Where only a single bladder vest system is provided, the second (bias) bladders components, transducer 60, valve A 56, valve B 58, valve C 62, and switch 76 are of course not present. In addition, the exhaust 78 of valve C 52 is blocked. The valve timing is similar to the two-bladder system, except that valve C now controls the pressure in the bladder during the deflation phase of the cycle. Instead of being actuated to remove vacuum from the bladder (FIG. 4), valve C is actuated to clamp the pressure at the desired low level. This desired level would be 5 to 30 mm Hg during cycles without ventilation, but less than or equal to zero during ventilation. Because of the above-noted delays between the electrical actuation signal and the mechanical actuation of the valve, a prediction algorithm has to be used to achieve the desired value of pressure. Since the deflation is non-linear, the linear method described above would be inaccurate. A piecewise-linear method is, therefore, used.

The timing of the valves (FIG. 4) is controlled by the background. The background is entered once every 4 ms, during which the cycle time counter is incremented, and the pressure prediction occurs. The B valves (FIGS. 3,4) are actuated when their stored "START TIME" values match the cycle time counter, starting the flow of high-pressure air through the open A valves and into the bladders. The A valves are then actuated when the stored "INFLATION" time values match the cycle time counter (prediction OFF), or at the appropriate predicted time (prediction ON), halting the flow of air into the bladders. The A, B, and C valves are all released when the stored "DUTY CYCLE" time values match the cycle time counter, starting vacuum-aided deflation of the bladders. The C valves are then actuated when the stored "VACUUM" time values match the cycle time counter, allowing the bladder pressures to return to atmospheric pressure.

Figure 8:
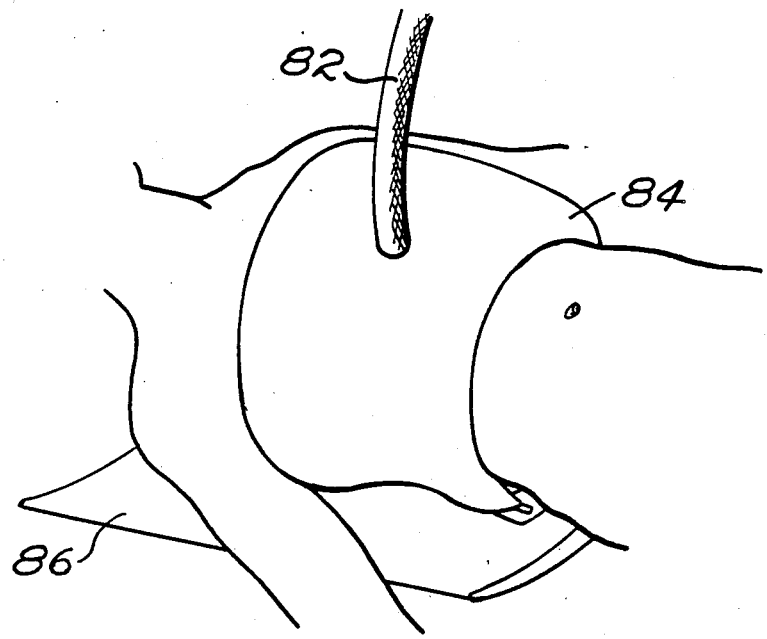
FIG. 8 shows an embodiment of the vest provided in accordance with the present invention.
Figure 9:
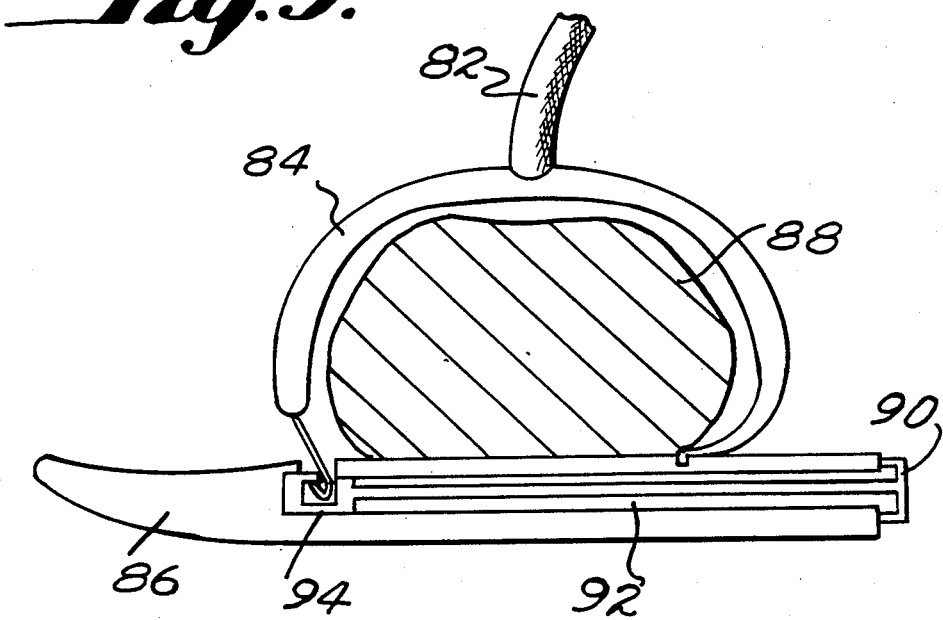
FIG. 9 is a schematic cross-sectional view of the vest of FIG. 8.
Figure 1:
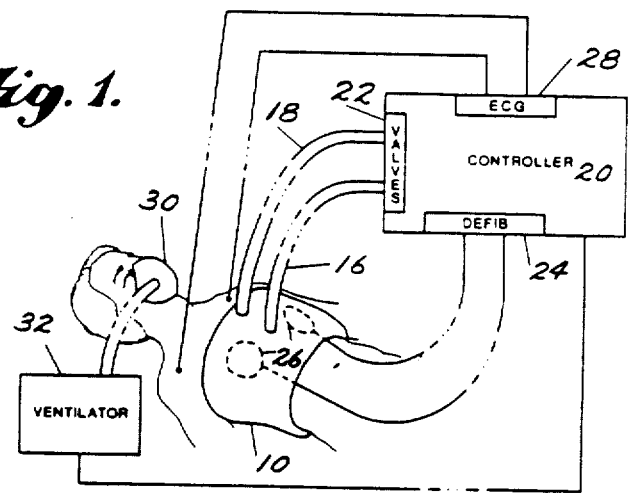
Figure 2:
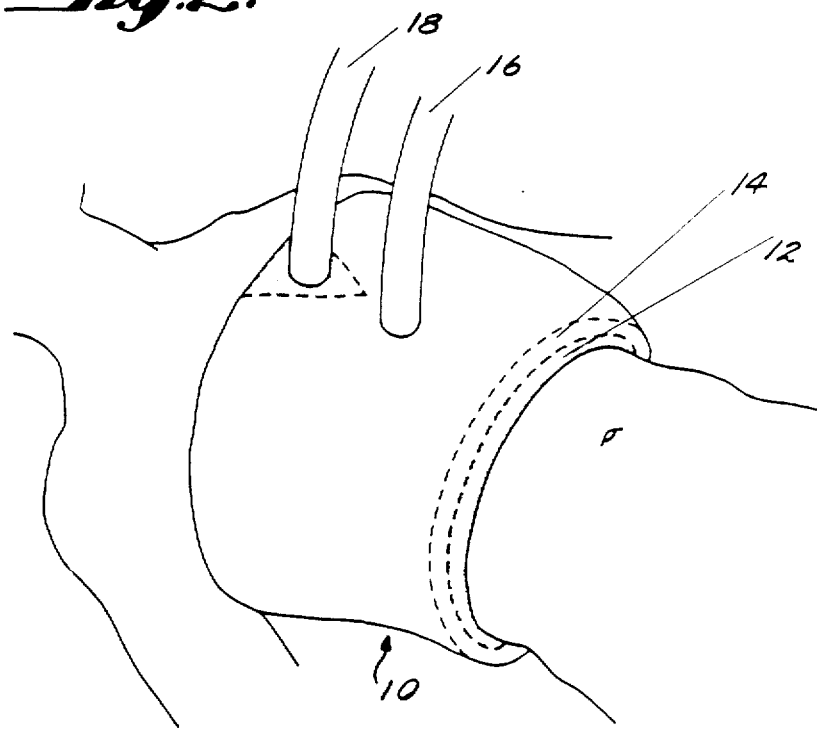
Figure 3:
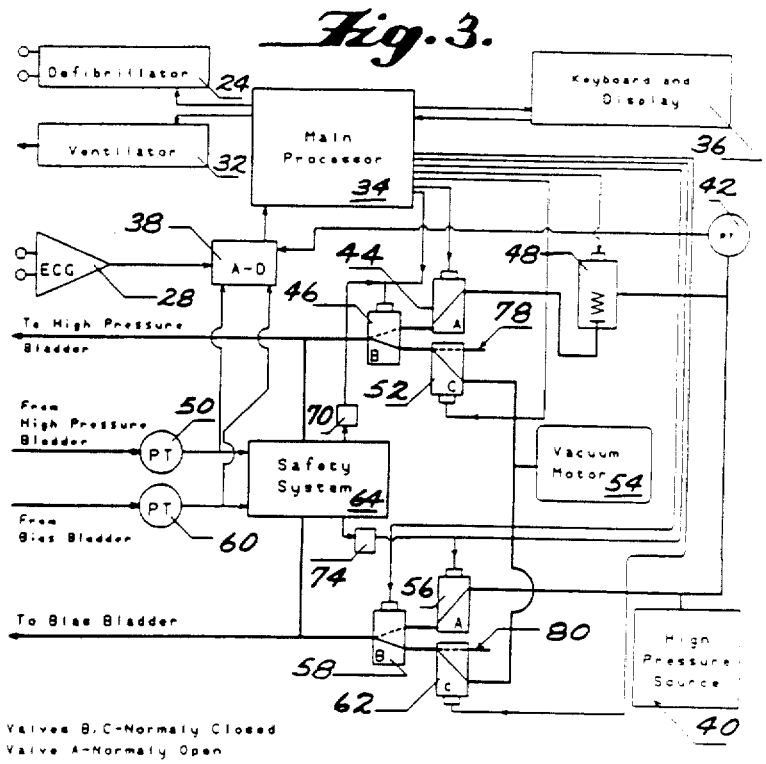
Figure 4:
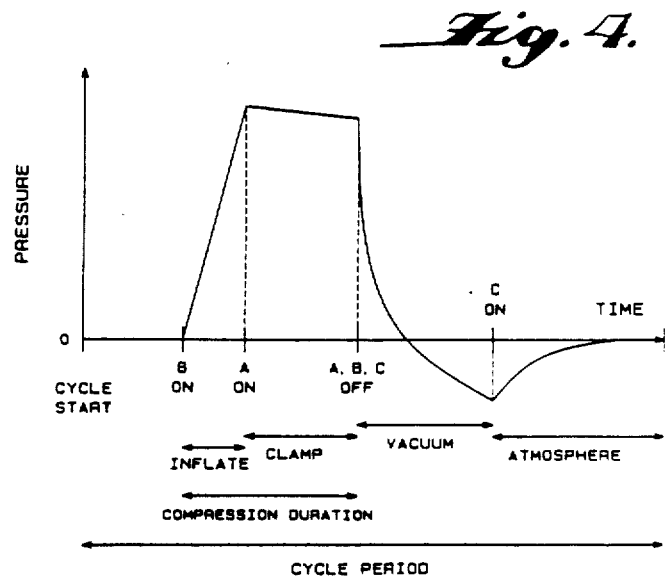
Figure 5:
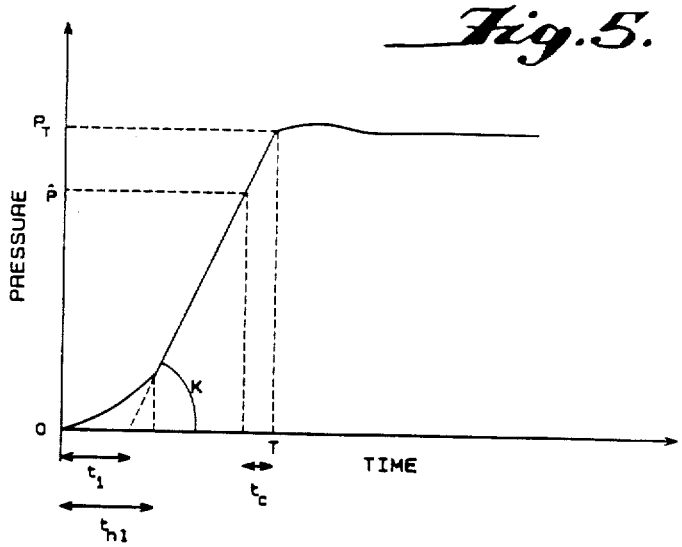
Figure 6:
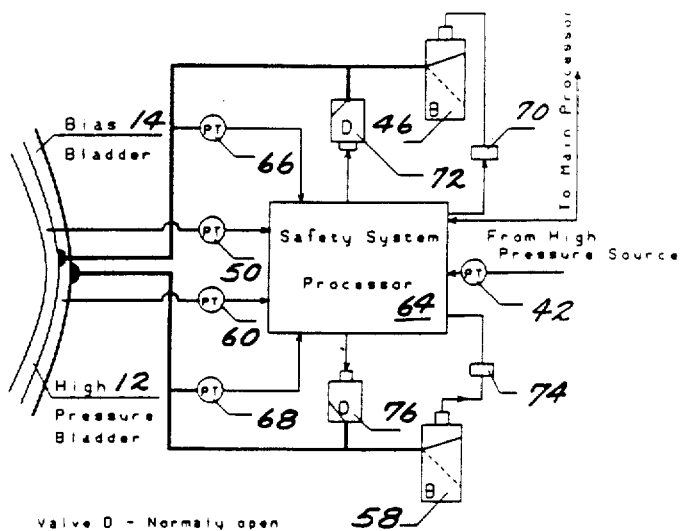

There are a number of vest designs that can be effectively used in accordance with the cardiopulmonary resuscitation and assisted circulation system of the present invention. The time needed to apply the vest can be minimized by providing a vest as shown for example in FIGS. 8 and 9. In that embodiment, one or more bladders 84 are connected by hose(s) 82 to the inflation system. A rigid base 86 can be rapidly slid under the patient's thorax 88 by one operator, without lifting the patient. One edge of the bladder(s) is permanently attached to the base as shown in FIG. 9. After the base is slide under the patent, the free end of the bladder(s) is placed over the patient's thorax and attached to the locking mechanism shown generally at 94 defined in the base. The base, therefore, is disposed underneath the patent and the bladders encircle most of the thorax. A handle 90 pulls a tightening mechanism through a channel 92 that can tighten the bladders about the thorax.

Another embodiment of the vest provided in accordance with the present invention is shown in FIG. 10. In that embodiment, different bladders 84, 98 are positioned partially on top of each other so that they cover different amounts of the thorax or abdomen. The pressure distribution on the thoracic surface can be changed by changing the relative positions of the bladders. As with the embodiment illustrated in FIGS. 8 and 9, the bladders are attached by respective hoses 82, 96 to the inflation system.

A third embodiment of a vest provided in accordance with the present invention is shown in FIG. 11. In this embodiment, any one bladder 84 can be modified to change its shape during inflation by adding an extra piece of material 100 to an edge of the bladder, such that it separates the upper surface of the bladder 102 from the lower surface of the bladder 104. The additional piece of material 100 can have properties different from those of the material making up the remainder of the bladder or can be pleated or varied in shape so as to make that edge bulge more or less than the other edges. As is apparent to the ordinary artisan, different edge configurations can be used to produce different amounts of compression at the edges of the vest assembly.

Referring to FIG. 12, since vacuum can be used to deflate the bladders, it is necessary to insure that the bladder material will not collapse over the hose opening and block the flow of air thereinto. Thus, a means for preventing blockage is provided in accordance with the present invention. In the embodiment illustrated in FIG. 12, a rigid cylindrical port 106 is attached to the bladder. The air hose 82 is attached to the port. The port extends into the bladder 84 and has holes 108 over its surface. Air as indicated by the arrows flows into and out of the bladder through the holes as well as through the open end of the cylinder. Air flow during deflation can not be blocked as the bladder material is sufficiently rigid that it cannot collapse around all of the holes provided on the connector 106.

As is apparent from the foregoing, both the one and two bladder vests formed in accordance with the present invention do not require ventilation either with simultaneous chest compression or with chest restriction in order to produce substantial changes in intrathoracic pressure. Furthermore, neither of the vests of the present invention need be applied too tightly or positioned with extreme accuracy as was the case with our earlier vest resuscitation system. Furthermore, the vest systems of the present invention produce large changes of intrathoracic pressure more consistently and at lower vest pressures than has previously been possible without compromising ventilation. The provision of feed-forward and feed-back control stabilize the peak vest pressure and can maintain intrathoracic pressure fluctuations relatively constant even when used to assist a failing heart with an irregular heart rhythm. The control of the pneumatic resistance of the inflow port of the high-pressure bladder enables independent control of the rise time of pressure and the novel sequencing of valves to optimize vest deflation in accordance with the present invention have an independent safety system to assure that vest pressure will not rise too high or be applied too long even during a malfunction of the inflation/deflation system. This is clearly a characteristic not heretofore realized.

Finally, while the one bladder system is mechanically simpler than the two bladder system, it can be appreciated that the one bladder vest system generates less intrathoracic pressure at any given level of vest pressure. Accordingly, the two bladder system while mechanically more complex is presently the most preferred embodiment of the present invention.

While the invention has been described in connection with what is presently considered to be the most practical and preferred embodiment, it is to be understood that the invention is not limited to the disclosed embodiment, but, on the contrary, it is intended to cover various modifications and equivalent arrangements included within the spirit and scope of the appended claims.

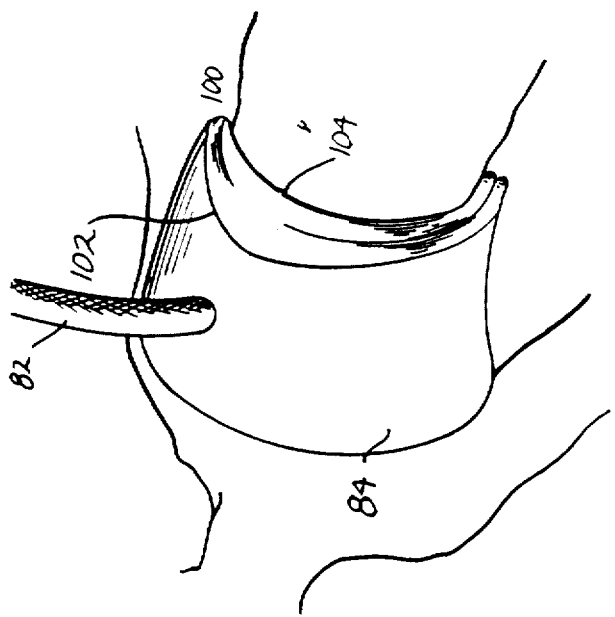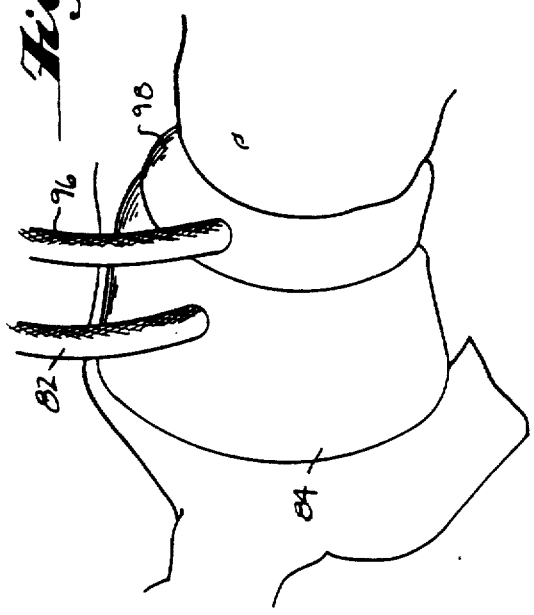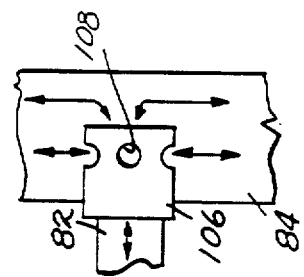

What is claimed is:

1. A system for generating cyclic fluctuations in intrathoracic pressure for use in cardiopulmonary resuscitation of a patient comprising:
   a first inflatable bladder means;
   means for cyclically inflating and deflating said inflatable bladder means;
   means for mounting said inflatable bladder means adjacent the chest wall of a patient so that cyclic inflation of deflation of the bladder means will produce pressure on the chest wall thus generating changes in intrathoracic pressure;
   means for (a) urging said inflatable bladder means against the chest wall of the patient to generate an initial pressure on the chest wall, (b) cyclically inflating said bladder means to generate large changes in intrathoracic pressure and, (c) periodically interrupting said urging to release said initial pressure and allow the chest to expand for adequate ventilation of the patient.

2. A system as in claim 1, wherein said means for urging the bladder means against the chest wall comprises means for clamping the pressure in the bladder means above atmospheric pressure such that said bladder means is cyclically inflated and deflated with the minimum pressure during an inflation and deflation cycle being above atmospheric pressure.

3. A system as in claim 1, wherein said means for cyclically urging comprises a second inflatable bladder means mounted so that said first inflatable bladder means is disposed intermediate the chest wall of the patient and the second bladder means and means for cyclically inflating and deflating said second bladder means whereby cyclic inflation of said second bladder means cyclically urges said first bladder means tightly against the chest wall and deflation of said second bladder means permits patient ventilation.

4. A system as in claim 3, wherein said means for cyclically inflating and deflating said second bladder means comprises a plurality of valve means and means for sequencing said valve means to inflate and deflate said second bladder means.

5. A system as in claim 3, wherein said means for mounting includes a vest-like garment having said first bladder means and said second bladder means mounted thereto and being adapted to be mounted in surrounding relation to the thorax of the patient.

6. A system as in claim 5, wherein said means for mounting further includes a rigid base member, said vest like garment having first and second opposite edges, a first edge of said vest-like garment being fixedly coupled to said rigid base member, said second edge of said vest-like garment including means for releasably coupling to a corresponding means for a coupling defined in said rigid base so that a thorax receiving cylindrical chamber is defined by said rigid base and said vest-like garment and further including means for varying the cross-sectional size of said cylindrical chamber.

7. A system as in claim 6, wherein said means for varying the cross-sectional size of said cylindrical chamber includes a channel defined within said rigid base member and a rod extending through said chamber and coupled to said means for coupling defined in said rigid base so that movement of said rod within said channel moves said means for coupling so as to move said second longitudinal edge toward and away from said rigid base member to thereby vary said cross-section of said cylindrical chamber.

8. A system as in claim 5 wherein said first and second bladder means of said vest-like garment are positioned so that different bladders cover different portions of the thorax or abdomen when applied to the patient and wherein the relative positions of the bladder means can be varied so as to vary the pressure distribution on the thoracic surface.

9. A system as in claim 5, wherein at least one of said bladder means has at least one edge formed of a material having properties distinct from the remainder of the bladder means so that said at least one edge bulges an amount different than the remainder of the bladder when inflated.

10. A system as in claim 5, wherein at least one edge of at least one of said bladder means is formed from a pleated material so that said edge will bulge more than the remainder of the bladder means so as to vary the amount of compression at the end of the bladder means.

11. A system as in claim 3 including primary means for monitoring pressure within said first bladder means, primary means for monitoring pressure within said second bladder means, and further, backup, monitoring means for monitoring pressure within said first and second bladder means, and means for actuating release of pressure from said bladder means if the pressure monitored by said backup monitoring means at least one of exceeds a predetermined maximum, exceeds a predetermined duration, or is different from the pressure monitored by either of the primary means for monitoring pressure.

12. A system as in claim 1, further comprising defibrillator means for delivering a defibrillating pulse to the chest wall of the patient.

13. A system as in claim 1, further comprising electrocardiogram processor means for receiving electrical signals from the chest wall of the patient and for synchronizing inflation and deflation of said first bladder means to the beating heart.

14. A system as in claim 1, further comprising means for conducting oxygen-enriched air to the patient.

15. A system as in claim 14, wherein said means for conducting includes a face mask and a source of oxygen-enriched air.

16. A system as in claim 1, wherein said means for mounting includes a vest-like garment having said first bladder means mounted thereto and being adapted to be mounted in surrounding relation to the thorax of the patient.

17. A system as in claim 16, wherein said means for mounting further includes a rigid base member, said vest like garment having first and second longitudinal side edges, a first longitudinal side edge of said vest-like garment being fixedly coupled to said rigid base member, said second longitudinal side edge of said vest-like garment including means for releasably coupling to a corresponding means for a coupling defined in said rigid base so that a thorax receiving cylindrical chamber is defined by said rigid base and said vest-like garment and further including means for varying the cross-sectional size of said cylindrical chamber.

18. A system as in claim 17, wherein said means for varying the size of said cylindrical chamber includes a channel defined within said rigid base member and a rod extending through said chamber and coupled to said means for coupling defined in said rigid base so that movement of said rod within said channel moves said means for coupling so as to move said second longitudinal edge toward and away from said rigid base member to thereby vary said cross-section of said cylindrical chamber.

19. A system as in claim 16, wherein said bladder means has at least one edge formed of a material having properties distinct from the remainder of the bladder means so that said edge bulges an amount different than the remainder of the bladder means when inflated.

20. A system as in claim 16, wherein at least one edge of said bladder means is formed from a pleated material so that said at least one edge will bulge more than the remainder of the bladder means so as to vary the amount of compression at the end of the bladder means.

21. A system as in claim 1, wherein said means for cyclically inflating and deflating said first bladder means comprises a plurality of valve means and means for sequencing said valves to inflate and deflate said first bladder means.

22. A system as in claim 21, further comprising means for monitoring pressure within said first bladder means, said means for monitoring pressure monitoring the rise in pressure during bladder inflation, at least one of said valves being actuated to clamp pressure in the bladder means at a predetermined level.

23. A system as in claim 22, wherein said means for actuating said valve applies an electrical signal to the valve at a time prior to the rise of bladder pressure to said predetermined level so that the time required for mechanical closure of the valve will be just sufficient for the pressure to rise to the desired level.

24. A system as in claim 23, including means for determining the time required for mechanical closure of the valve sufficient for pressure to rise to the desired level.

25. A system as in claim 21, wherein said valve means comprise solenoid valves.

26. A system as in claim 1, further comprising means for monitoring pressure within said first bladder means.

27. A system as in claim 1, further including means for varying the rate of flow of inflating air to said first bladder means.

28. A system as in claim 27, wherein said means for varying includes a variable resistor.

29. A system as in claim 1, wherein said means for cyclically inflating and deflating said bladder means includes an air-hose element coupled to said inflatable bladder means, the coupling of said hose to said bladder means including a substantially rigid coupling element having a first end coupled to said air hose and a second open end defined within said bladder means and further including at least one aperture defined transversely to said second open end.

30. A system for generating cyclic fluctuations in intrathoracic pressure for use in cardiopulmonary resuscitation of a patient comprising:
a first inflatable bladder means covering the front of the chest and extending laterally to cover the sides;
means for cyclically inflating and deflating said inflatable bladder means;
means for mounting said inflatable bladder means adjacent the chest wall of a patient so that cyclic inflation of deflation of the bladder means will produce pressure on the chest wall thus generating changes in intrathoracic pressure;
means for urging said inflatable bladder means against the chest wall of the patient so that cyclic inflation of the bladder means generates large changes in intrathoracic pressure and for periodically interrupting said urging so that the chest can expand for adequate ventilation of the patient.

* * * * *

UNITED STATES PATENT AND TRADEMARK OFFICE
CERTIFICATE OF CORRECTION

PATENT NO. : 4,928,674
DATED : May 29, 1990
INVENTOR(S) : Henry Halperin, et al.

It is certified that error appears in the above-identified patent and that said Letters Patent is hereby corrected as shown below:

In the Drawings

Figs. 2, 4, 6, 7 and 12 in sheets 1, 2, 3, 4 and 6, should appear as shown on the attached sheets.

Column 5, line 30, the formula should appear as follows:
--$p = \hat{P} = P_T - K \cdot t_C + \omega$ Signed and Sealed this Fourth Day of February, 1992

Attest:

HARRY F. MANBECK, JR.

*Attesting Officer*  *Commissioner of Patents and Trademarks*

Fig. 7

| Prediction ON | Combined ON | B Bladder ON | | | HP Bladder ON | Assistance OFF | Ventilation ON |
|---|---|---|---|---|---|---|---|
| | | OLD | NEW | | REAL | | |
| RATE (/min) | | 60 | 60 | | | | |
| DUTY CYCLE (%) | | 50 | 50 | | | | |
| START TIME (%) | | 0 | 0 | | | | |
| INFLATION (ms) | | 110 | 110 | | 112 | | |
| VACUUM (ms) | | 200 | 200 | | | | |
| PRESSURE (mm Hg) | | 190 | <u>190</u> | | 195 | | |
| VENT.DURATION (ms) | | 500 | 500 | | | | |
| VENT.START (%) | | 5 | 5 | | | | |

| | | | | | | | |
|---|---|---|---|---|---|---|---|
| RATE (/min) | | 60 | 60 | | | | |
| DUTY CYCLE (%) | | 50 | 50 | | | | |
| START TIME (%) | | 0 | 0 | | | | |
| INFLATION (ms) | | 40 | 40 | | | | |
| VACUUM (ms) | | 200 | 200 | | | | |
| PRESSURE (mm Hg) | | 15 | 15 | | 18 | | |
| RELEASE RATE (cyc) | | 5 | 5 | | | | |

| COMBINED | B.BLAD | CHANGE | HP BLAD | PREDICT | SYNCHRO | ASSIST | VENT. |
|---|---|---|---|---|---|---|---|
| A | B | C | D | E | F | G | H |